United States Patent [19]

Urdea et al.

[11] Patent Number: 5,367,066

[45] Date of Patent: Nov. 22, 1994

[54] OLIGONUCLEOTIDES WITH SELECTABLY CLEAVABLE AND/OR ABASIC SITES

[75] Inventors: Michael S. Urdea, Alamo; Thomas Horn, Berkeley, both of Calif.

[73] Assignee: Chiron Corporation, Emeryville, Calif.

[21] Appl. No.: 736,445

[22] Filed: Jul. 24, 1991

Related U.S. Application Data

[63] Continuation-in-part of Ser. No. 559,961, Jul. 27, 1990, which is a continuation-in-part of Ser. No. 398,711, Aug. 25, 1989, abandoned, which is a continuation-in-part of Ser. No. 251,152, Sep. 29, 1988, Pat. No. 5,118,605, which is a continuation-in-part of Ser. No. 661,508, Oct. 16, 1984, Pat. No. 4,775,619.

[51] Int. Cl.$^5$ .................. C07H 21/04; C07H 21/00
[52] U.S. Cl. .................. 536/24.3; 536/24.31; 536/24.32; 435/6
[58] Field of Search .............. 536/27, 23.1, 24.3, 536/24.31, 24.32; 435/6

[56] References Cited

U.S. PATENT DOCUMENTS

| | | | |
|---|---|---|---|
| 4,415,732 | 11/1983 | Caruthers et al. | 536/27 |
| 4,725,537 | 2/1988 | Fritsch et al. | 435/6 |
| 4,775,619 | 10/1988 | Urdea | 435/6 |
| 4,876,187 | 10/1989 | Bender et al. | 435/6 |

FOREIGN PATENT DOCUMENTS

| | | |
|---|---|---|
| 0142299 | 5/1985 | European Pat. Off. . |
| 0227976 | 7/1987 | European Pat. Off. . |
| WO83/02277 | 7/1983 | WIPO . |
| WO88/01302 | 2/1988 | WIPO . |

OTHER PUBLICATIONS

Peoc'h et al. Tetrahedron Letters 32(2):207–210, 1991.
Alwine et al., *Proc. Natl. Acad. Sci.* (1977) 74(12):5350–5354.
Ashly et al., *Anal. Biochem.* (1984) 140:95–103.
Bauman et al., *J. Histochem. Cytochem.* (1981) 29(12):227–237.
Beaucage et al., *Tetrahedron Letters* (1981) 22(20):1859–1862.
Belagaje et al., *Nucleic Acids Res.* (1982) 10(20):6925–6303.
Bischofberger et al., *Nucl. Acids Res.* (1987) 15(2):709–716.
Chou et al., *New Engl. J. Med.* (1983) 308(16):921–925.
Cramer et al., *Angew. Chem. Int. Ed. Engl.* (1968) 7(6):473–474.
de Napole et al., *Gazz. Chim. Ital.* (1984) 114:65–68.
Dreyer et al., *Chem. Abstracts* (1985) 102(21):302 (abstract no. 181866e).
Gait et al., *Nucleic Acids Res.* (1977) 4(4):1135–1158.
Groebke et al., *Helvetica Chemica Acta* (1990) 73:608–617.
Hayatsu et al., *J. Am. Chem. Soc.* (1957) 89:3880–3887.
Hebert et al., *Can. J. Chem.* (1974) 52:187–189.
Ho et al., *Biochemistry* (1981) 20:64–67.
Horn et al., *Tetrahedron Letters* (1986) 27(39):4705–4708.
Horn et al, *DNA* (1986) 5(5):421–426.
Leary et al., *Proc. Natl. Acad. Sci.* (1983) 80:4045–4049.
Matteucci et al., *J. Am. Chem. Soc.* (1991) 103:3185–3191.
Meinkoth et al., *Anal. Biochem.* (1984) 138:267–284.
Pfeuffer et al., *J. Biol. Chem.* (1975) 250(3):867–876.
Ranki et al., *Gene* (1983) 21:77–85.
Renz et al., *Nucl. Acids Res.* (1984) 12(8):3435–3444.
Rosenthal et al., *Tetrahedron Letters* (1983) 24(16):1691–1694.
Warner et al., *DNA* (1984) 3(5):401–411.

*Primary Examiner*—Johnnie R. Brown
*Assistant Examiner*—Gary L. Kunz
*Attorney, Agent, or Firm*—Reed & Robins

[57] ABSTRACT

A modified polynucleotide containing at least one cleavable or abasic site as shown below.

(Abstract continued on next page.)

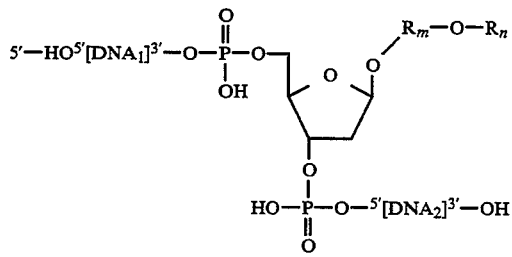

DNA₁ is a first segment of DNA; DNA₂ is a second segment of DNA; and $R_m$ is $C_1$ to $C_{16}$ alkylene or an oxytheylene oligomer $-(CH_2CH_2O)_z-$ where z is an interger in the range of 1 to 16 inclusive, and $R_n$ is selected from the group consisting of

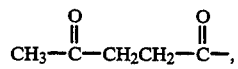

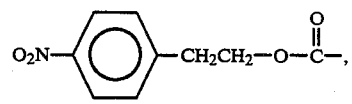

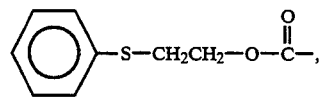

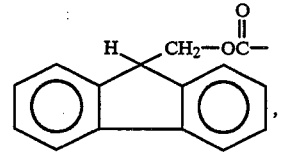

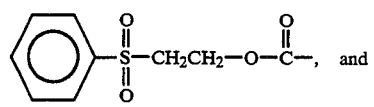

$CH_3O-CH_2-CH_2-O-CH_2-$.

Such polynucleotides are useful in solid phase hybridizations because they permit the release of a label from the solid support after the hybridization reaction.

23 Claims, No Drawings

OLIGONUCLEOTIDES WITH SELECTABLY CLEAVABLE AND/OR ABASIC SITES

CROSS-REFERENCE TO RELATED APPLICATIONS

This application is a continuation-in-part of U.S. patent application Ser. No. 07/559,961, filed Jul. 27, 1990, which is a continuation-in-part of U.S. patent application Ser. No. 07/398,711, filed Aug. 25, 1989, now abandoned, which is a continuation-in-part of U.S. patent application Ser. No. 07/251,152, filed Sep. 29, 1988, now U.S. Pat. No. 5,118,605 issued on Jun. 2, 1992, which is a continuation-in-part of U.S. patent application Ser. No. 06/661,508, filed Oct. 16, 1984 and issued Oct. 4, 1988 as U.S. Pat. No. 4,775,619.

TECHNICAL FIELD

The invention relates generally to the incorporation of selectably cleavable and/or abasic sites into oligonucleotide chains, and more particularly relates to novel reagents useful for those purposes. The invention also relates to methods of using the novel reagents in biochemical assays and in phosphorylation reactions.

BACKGROUND

Incorporation of selectably cleavable sites into oligonucleotide and polynucleotide chains has been described in related U.S. patent application Ser. No. 251,152, issued as U.S. Pat. No. 5,118,605 on Jun. 2, 1992, and in great-grandparent U.S. Pat. No. 4,775,619, the disclosures of which are incorporated by reference herein. Selectably cleavable sites are useful in a number of different types of hybridization assay formats. For example, in one type of assay in which hybridization gives rise to a solid-supported duplex of a labeled probe and sample DNA, a selectably cleavable site contained within the hybrid structure will enable ready separation of the label from the solid support. U.S. Pat. No. 4,775,619 is primarily directed to the use of restriction endonuclease-cleavable sites in such assays, while application Ser. No. 251,152, issued as U.S. Pat. No. 5,118,605 on Jun. 2, 1992, concerns chemically cleavable sites, e.g., disulfide linkages, 1,2-diols, and the like. These chemically cleavable sites can be introduced during oligonucleotide synthesis, and are cleavable with particular chemical reagents, e.g., with thiols, periodate, or the like.

The present invention is also directed to selectably cleavable sites. However, the present method involves introduction of sites which are cleavable by photolysis as well as sites which are cleavable by other means, e.g., using chemical or enzymatic reagents, e.g., reducing agents. The cleavable sites of the invention are created by incorporation of chemical moieties, preferably photolabile moieties, into oligonucleotide or polynucleotide chains. The novel photolabile moieties are useful in a number of different types of hybridization assay formats, including those described in the above-cited applications, as well as in the amplification nucleic acid hybridization assay described in co-pending, commonly assigned U.S. patent application Ser. No. 252,638, filed Sep. 30, 1988, (now abandoned) also incorporated by reference herein.

Another use of the reagents of the invention is, in general terms, the creation of abasic sites within oligonucleotides. By "abasic site" is meant an ether moiety —OR at a position which normally contains a hydroxyl group —OH or a nucleobase. The utility of such derivatization is extensive as will be disclosed in detail hereinbelow.

Still another use of the reagents of the invention is in chemical phosphorylation. In many different aspects of oligonucleotide chemistry, chemical phosphorylation of hydroxyl groups is necessary. For example, in oligonucleotide synthesis, after synthesis and deprotection, the free 5'-hydroxyl group of the oligonucleotide must be phosphorylated for use in most biological processes. Also, phosphorylation of the 3'-hydroxyl functionality is necessary: (1) to prevent extension of the 3' terminus by a polymerase; and (2) in the chemical ligation of DNA, i.e., a 3' phosphate moiety is typically required in the coupling of oligonucleotides using chemical means.

5'-phosphorylation has conventionally been carried out with T4 polynucleotide kinase and ATP, a reaction that is not particularly reliable or efficient. Several methods for chemical 5'-phosphorylation are also known, including those described by Nadeaux et al., *Biochemistry* 23:6153–6159 (1984), van der Marel et al., *Tetrahedron Lett.* 22:1463–1466 (1981), Himmelsbach and Pfleiderer, *Tetrahedron Letters* 23:4793–4796 (1982), Marugg et al., *Nucleic Acids Research* 12:8639–8651 (1984), and Kondo et al., *Nucleic Acids Research Symposium Series* 16:161–164 (1985). However, most of these methods involve the use of unstable reagents or require extensive modification of standard deprotection and purification procedures. Similar problems have been found with monofunctional and bifunctional 3'-phosphorylating reagents (see Sonveaux, supra, at 297).

Thus, in addition to utility in providing cleavable and/or abasic sites within oligonucleotide or polynucleotide chains, many of the compounds of the present invention are additionally useful as phosphorylating reagents which overcome the limitations of current phosphorylation procedures (and may also be useful in phosphorylation reactions that are used in conventional dimethoxytrityl [DE] purification schemes).

DESCRIPTION OF THE PRIOR ART

Background references which relate generally to methods for synthesizing oligonucleotides include those related to 5'-to-3' syntheses based on the use of β-cyanoethyl phosphate protecting groups, e.g., de Napoli et al., *Gazz Chim Ital* 114:65 (1984), Rosenthal et al., *Tetrahedron Letters* 24:1691 (1983), Belagaje and Brush, *Nucleic Acids Research* 10:6295 (1977), in references which describe solution-phase 5'-to-3' syntheses include Hayatsu and Khorana, *J American Chemical Society* 89:3880 (1957), Gait and Sheppard, *Nucleic Acids Research* 4:1135 (1977), Cramer and Koster, *Angew. Chem. Int. Ed. Engl.* 7:473 (1968), and Blackburn et al., *Journal of the Chemical Society*, Part C, 2438 (1967).

In addition to the above-cited art, Matteucci and Caruthers, *J. American Chemical Society* 102:3185–3191 (1981), describe the use of phosphochloridites in the preparation of oligonucleotides. Beaucage and Caruthers, *Tetrahedron Letters* 1:1859–1862 (1981), and U.S. Pat. No. 4,415,732 describe the use of phosphoramidites in the preparation of oligonucleotides. Smith, *ABL* 15–24 (December 1983), describes automated solid-phase oligodeoxyribonucleotide synthesis. See also the references cited therein, and Warner et al., *DNA* 3:401–411 (1984), whose disclosure is incorporated herein by reference.

Horn and Urdea, *DNA* 5.5:421–425 (1986), describe phosphorylation of solid-supported DNA fragments using bis(cyanoethoxy)-N,N-diisopropyl-aminophosphine. See also, Horn and Urdea, *Tetrahedron Letters* 27:4705–4708 (1986).

References which relate to hybridization techniques in general include the following: Meinkoth and Wahl, *Anal. Biochemistry* 138:267–284 (1984), provide an excellent review of hybridization techniques. Leafy et al., *Proc. Natl. Acad. Sci.* (USA) 80:4045–4049 (1983), describe the use of biotinylated DNA in conjunction with an avidin-enzyme conjugate for detection of specific oligonucleotide sequences. Ranki et al., *Gene* 21:77–85, describe what they refer to as a "sandwich" hybridization for detection of oligonucleotide sequences. Pfeuffer and Helmrich, *J. Biol. Chem*, 250:867–876 (1975), describe the coupling of guanosine-5'-O-(3-thiotriphosphate) to Sepharose 4B. Bauman et al., *J. Histochem. and Cytochem.* 29:227–237, describe the 3'-labeling of RNA with fluorescers. PCT Application WO/8302277 describes the addition to DNA fragments of modified ribonucleotides for labeling and methods for analyzing such DNA fragments. Renz and Kurz, *Nucl. Acids. Res.* 12:3435–3444, describe the covalent linking of enzymes to oligonucleotides. Wallace, *DNA Recombinant Technology* (Woo, S., ed.) CRC Press, Boca Raton, Fla., provides a general background of the use of probes in diagnosis. Chou and Merigan, *N. Eng. J. of Med.* 308:921–925, describe the use of a radioisotope-labeled probe for the detection of CMV. Inman, *Methods in Enzymol.* 34B, 24:77–102 (1974), describes procedures for linking to polyacrylamides, while Parikh et al., *Methods in Enzymol*, 34B, 24:77–102 (1974), describe coupling reactions with agarose. Alwine et al., *Proc. Natl. Acad. Sci.* (USA) 74:5350–5354 (1977), describe a method of transferring oligonucleotides from gels to a solid support for hybridization. Chu et al., *Proc. Natl. Acad. Sci.* (USA) 11:6513–6529, describe a technique for derivatizing terminal nucleotides. Ho et al., *Biochemistry* 20:64–67 (1981), describe derivatizing terminal nucleotides through phosphate to form esters. Ashley and MacDonald, *Anal. Biochem.* 140:95–103 (1984), report a method for preparing probes from a surface-bound template.

Hebert and Gravel, *Can. J. Chem.* 52:187–189 (1974), and Rubinstein et al., *Tetrahedron Lett.*, No. 17, pp. 1445–1448 (1975), describe the use of 2-nitrophenyl-containing compounds as light-sensitive protecting groups.

K. Groebke et al. *Helvetica Chemica Acta.* 73:608–617 (1990) is relevant insofar as the reference describes the use of the t-butyldimethylsilyl moiety to protect a hydroxyl functionality.

SUMMARY OF THE INVENTION

Accordingly, it is a primary object of the invention to address the above-mentioned needs in the art, and to provide methods and reagents for introducing selectably cleavable and/or abasic sites into oligonucleotide chains.

It is another object of the invention to provide such methods and reagents for introducing selectably cleavable sites into oligonucleotide chains, wherein the selectably cleavable sites are chemically cleavable.

It is still another object of the invention to provide such methods and reagents for introducing selectably cleavable sites into oligonucleotide chains, wherein the selectably cleavable sites are cleavable by light.

It is a further object of the invention to provide methods and reagents for introducing abasic sites into oligonucleotide chains.

It is still a further object of the invention to provide methods and reagents for chemically phosphorylating hydroxyl groups.

It is yet another object of the invention to provide reagents for incorporating abasic sites into oligonucleotide chains which may then be used to create a branched nucleic acid multimer.

It is another object of the invention to provide such reagents wherein the abasic sites are non-nucleotidic.

Additional objects, advantages and novel features of the invention will be set forth in part in the description which follows, and in part will beccome apparent to those skilled in the art upon examination of the following, or may be learned by practice of the invention.

In one aspect, then, novel reagents are provided which are photolabile chemical compounds having the general structure

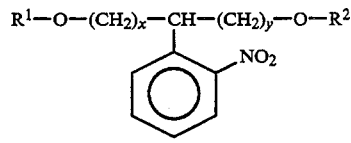

wherein $R^1$ $R^2$, x and y are as defined below. These compounds may be incorporated into oligonucleotide chains so as to enable cleavage by light.

In another aspect, novel reagents are provided having the general structure

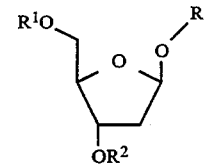

wherein $R^1$ $R^2$ and R are as defined below Such compounds are useful in creating abasic sites within oligonucleotide chains, which may or may not be cleavable.

In still another aspect, novel reagents are provided having the general structure

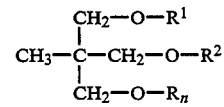

wherein $R^1$, $R^2$ and $R_n$ are as defined below Such compounds are useful to create branch points in the synthesis of nucleic acid multimers.

In other aspects, methods of using these reagents in a variety of contexts are provided as well.

DETAILED DESCRIPTION OF THE INVENTION

A. Definitions:

By "selectably cleavable site" is meant a functionality or plurality of functionalities which can be selectively cleaved. The focus of the present invention, as noted hereinabove, is primarily on sites which are specifically cleavable using photolysis.

As used herein the terms "oligonucleotide" and "polynucleotide" shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine base, or of a modified purine or pyrimidine base. The term "nucleoside" will similarly be generic to ribonucleosides, deoxyribonu cleosides, or to any other nucleoside which is an N-glycoside of a purine or pyrimidine base, or of a modified purine or pyrimidine base. There is no intended distinction in length between the term "oligo nucleotide" and "polynucleotide" and these terms will be used inter changeably. These oligonucleotides and polynucleotides may be single-stranded or double-stranded, typically single-stranded. Also, the oligonucleotides of the present invention are normally of from about 2 to about 2000 monomer units, and more typically, for most probe-based applications, from about 2 to about 100 monomer units.

By "nucleic acid sample" is intended a sample suspected of containing a nucleic acid sequence of interest.

By "nucleic acid analyte" is intended DNA or RNA in said nucleic acid sample containing the sequence of interest.

By "phosphorylating reagents" as used herein are intended compounds which, upon a reaction or series of reactions with a hydroxyl-containing compound, will yield a phosphate monoester.

By "lower alkyl" and "lower alkoxy" are meant alkyl and alkoxy substituents, respectively, having from about 1 to 8, more typically from about 1 to 6, carbon atoms.

Where aromatic substituents are indicated, it is to be understood that each individual aromatic ring may be substituted at one or more carbon atoms with moieties which do not substantially affect function or reactivity.

B. Structure of the Novel Photolabile Reagents:

In one embodiment of the invention, novel reagents are provided which are photolabile chemical compounds having the structure:

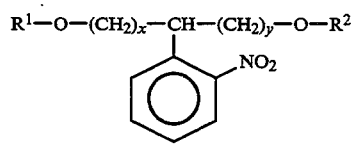

wherein $R^1$ is a base-stable, acid-sensitive blocking group, $R^2$ is a phosphorus derivative selected to enable addition of the reagent to the 5' position of a nucleoside or an oligonucleotide chain, and one of x and y is zero while the other is an integer in the range of 1 to 12 inclusive. Two basic types of structures fall within the above generic formula: (1) those wherein x is nonzero and y is zero (sometimes referred to herein as "NP1-type" reagents); and (2) those wherein x is zero and y is nonzero (sometimes referred to herein as "NP2-type"-reagents). These two types of structures are, as may be readily inferred from the above generic formula, quite similar. They are each useful for introducing specific sites into oligonucleotide chains, which, because of the nitrophenyl moiety, are readily cleavable via photolysis. However, as will be discussed in more detail below, the two families of chemical reagents are distinguishable insofar as they are useful in slightly different contexts.

Turning now in more detail to the various substituents of the novel photolabile reagents:

$R^1$ is, as noted above, a base-stable, acid-sensitive blocking group. Such blocking groups are well known in the art of oligonucleotide synthesis and include unsubstituted or substituted aryl or aralkyl groups, where the aryl is, e.g., phenyl, naphthyl, furanyl, biphenyl, or the like, and where the substituents are from 0 to 3, usually 0 to 2, and include any non-interfering stable groups, neutral or polar, electron-donating or withdrawing. Examples of such groups are dimethoxytrityl (DMT), monomethoxytrityl (MMT), trityl and pixyl. A particularly preferred moiety for use herein is DMT.

$R^2$ is a phosphorus derivative which is selected so as to facilitate condensation of the reagent with the 5'-hydroxyl group of a nucleoside or an oligonucleotide chain. Such groups include phosphoramidites, phosphotriesters, phosphodiesters, phosphites, H-phosphonates, phosphorothioates, and the like (see, e.g., EP Publication No. 0225807 by Urdea et al., "Solution Phase Nucleic Acid Sandwich Assay and Polynucleotide Probes Useful Therein" the disclosure of which is incorporated by reference herein). Particularly preferred groups useful as $R^2$ are phosphoramidites having the structure:

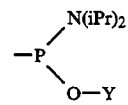

wherein Y is selected from the group consisting of methyl and β-cyanoethyl, and "iPr" represents isopropyl. Most preferably, Y is β-cyanoethyl.

As may be readily deduced from the above definitions, the $R^1$ and $R^2$ substituents are generally selected so as to allow incorporation of the photolabile reagent into a DNA fragment using standard phosphoramidite chemistry protocols. That is, during oligonucleotide synthesis, the $R^2$ substituent is selected so as to react with the 5'-hydroxyl group of a nucleoside or an oligonucleotide chain, while the $R^1$ moiety is selected so as to enable reaction with the 3'-hydroxyl of a nucleoside or an oligonucleotide chain.

With respect to the subscripts x and y, one of x and y is zero while the other is an integer in the range of 1 to 12 inclusive, more preferably in the range of 1 to 4 inclusive, and most preferably 1.

Exemplary reagents falling within the aforementioned general category are the following:

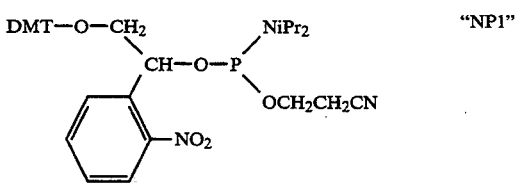

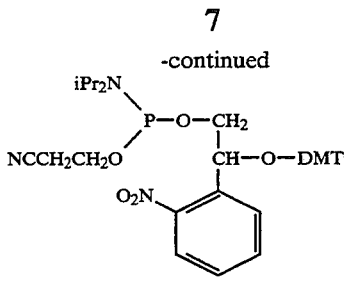
"NP2"

As indicated, these specific structures, [2-(2-nitrophenyl)-2-(0-dimethoxytrityloxy)ethoxy]-N,N-diisopropylamino-2-cyanoethoxyphosphine and [2-(2-nitrophenyl)-1-(0-dimethoxytrityloxy)ethoxy]-N,N-diisopropylamino-2-cyanoethoxyphosphine, are designated herein as compounds "NP1" and "NP2" respectively, and are the specific reagents synthesized in Examples 1 and 2 below.

C. Synthesis of the Above Reaqents:

Reagents of NP1-type, that is, wherein x is nonzero and y is zero, are synthesized according to the reaction sequence outlined in Scheme 1. Reagents of the NP2-type are synthesized according to the set of reactions outlined in Scheme 2.

Scheme 1

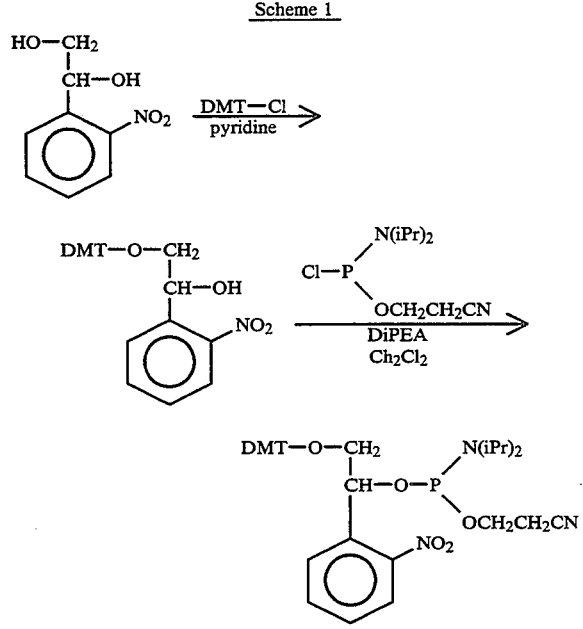

Scheme 2

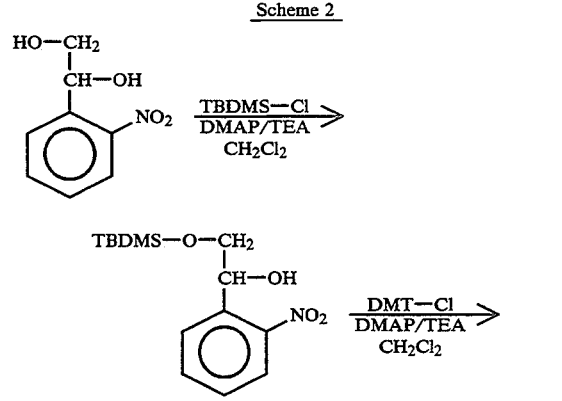

-continued
Scheme 2

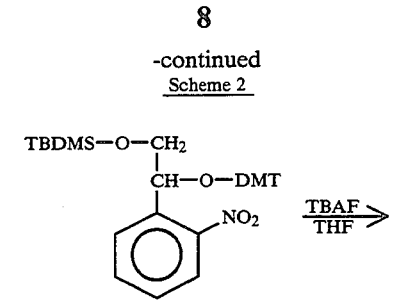

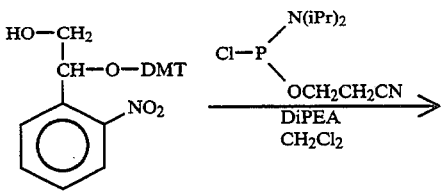

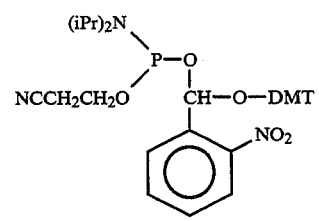

Abbreviations in Schemes 1 and 2: "DMT"=dimethoxytrityl; "DMT-Cl"=dimethoxytrityl chloride; "iPr-'"=isopropyl; "DiPEA"=diisopropylethylamine; "TBDMS-Cl"=t-butyldimethylsilyl chloride; "DMAP"=4-dimethylaminopyridine; "TEA"=triethylamine; "TBAF"=tetrabutylammonium fluoride.

Synthesis of NP1-type reagents involves capping the terminal hydroxyl group of 2-(O-nitrophenyl)-1,2-ethanediol with the $R^1$ species, e.g., with DMT or the like, followed by reaction of the remaining hydroxyl group with a selected phosphorus derivative to give rise to the $R^2$ moiety. As shown in Scheme 1, an exemplary reagent for this latter purpose is chloro-N,N-diisopropylamino-2-cyanoethoxyphosphine. Variations on this basic scheme may be readily deduced. For example, to provide different $R^1$ substituents, one would use monomethoxytrityl chloride, trityl chloride, pixyl chloride, or the like, as an alternative to dimethoxytrityl chloride. Similarly, to give rise to different $R^2$ substituents, alternative substituted phosphines would be employed in the second step of the reaction. To vary x, additional methylene groups are required in the initial starting material.

To synthesize reagents of the NP2-type, i.e., wherein x is zero and y is nonzero, a similar synthetic sequence is carried out, except that the order in which the $R^1$ and $R^2$ substituents are introduced is reversed. Thus, initially, the terminal hydroxyl group of the 2-(O-nitrophenyl)-1,2-ethanediol starting material is reacted with t-butyldimethylsilyl chloride ("TBDMS-Cl") to block that hydroxyl group during the next reaction step, in which the remaining free hydroxyl group, is reacted with a base-stable, acid-sensitive blocking group, e.g., dimethoxytrityl chloride ("DMT-Cl"), to provide the $R^1$ substituent. The terminal hydroxyl group is then deprotected, e.g., with tetrabutylammonium fluoride, and, as in Scheme 1, reacted with a suitable substituted phosphine derivative to give rise to the $R^2$ moiety.

D. Use of the Above Reagents to Create Selectably Cleavable Sites

The novel photolabile reagents of the invention are readily incorporated into an oligonucleotide or polynucleotide chain using standard phosphoramidite chemistry, well known in the art, and as described, for example, in a number of the references cited hereinabove. In general terms, incorporation of the novel reagent into a DNA fragment involves linkage to a 5'-hydroxyl group at $R^2$, and linkage to a 3'-hydroxyl group at $R^1$.

Thus, after incorporation of the photolabile reagent, the hybrid oligonucleotide chain will have the following structure:

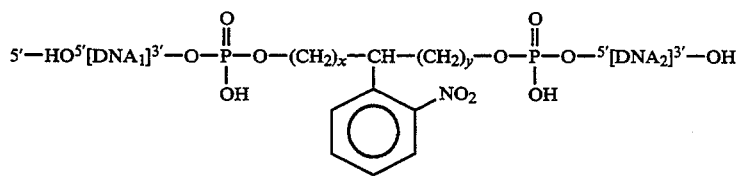

in which $DNA_1$ represents a first segment of DNA, $DNA_2$ represents a second segment of DNA, and x and y are as defined earlier. $DNA_1$ and $DNA_2$ may be either linear or branched. This polynucleotide reagent may be used in hybridization assays such as those described in parent application Serial No. 251,152, issued as U.S. Pat. No. 5,118,605 on Jun. 2, 1992 and grandparent U.S. Pat. No. 4,775,619. These assays involve the use of linear polynucleotide reagents having selectable cleavage sites, i.e., wherein $DNA_1$ and $DNA_2$ are linear. The polynucleotide reagent containing the photolabile moiety of the invention may also be used in the amplification assays of U.S. patent applications Serial Nos. 07/252,638 (now abandoned) and 07/340,031, issued as U.S. Pat. No. 5,124,246 on Apr. 18, 1989, both incorporated by reference herein (see also PCT Publication No. WO89/03891). As described in those applications, cleavable "linker" molecules may be incorporated into amplification multimers at predetermined sites for the purpose of analyzing the structure of the multimer or as a means for releasing predetermined segments (such as the portion of the multimer that binds to the labeled oligonucleotide). In such an application $DNA_1$ and/or $DNA_2$ are branched polynucleotide segments. Subsequent to multimer synthesis and purification, the branched polynucleotide structure of the multimer can be cleaved specifically without additional degradation of the nucleotide structure. It is preferred, clearly, that the cleavable sites be introduced at or near the junctions of the multimer to enable quantitation of the individual multimer "branches".

Depending on whether the photolabile reagent incorporated into the oligonucleotide or polynucleotide is an NP1-type (i.e., wherein x is nonzero and y is zero) or an NP2-type (i.e., wherein x is zero and y is nonzero), two different types of fragments will result upon cleavage. That is, as illustrated in Scheme 3, cleavage of an oligonucleotide containing an NP1-type moiety will result in a first fragment having a terminal 5'-phosphate and a second fragment which at its 3'-terminus contains the residue 2-nitrosophenyl species. By contrast, as illustrated in Scheme 4, cleavage of a polynucleotide containing the NP2-type moiety will give rise to a first fragment containing the residual 2-nitrosophenyl group at its 5' terminus and a second fragment having a terminal 3'-phosphate.

Scheme 3

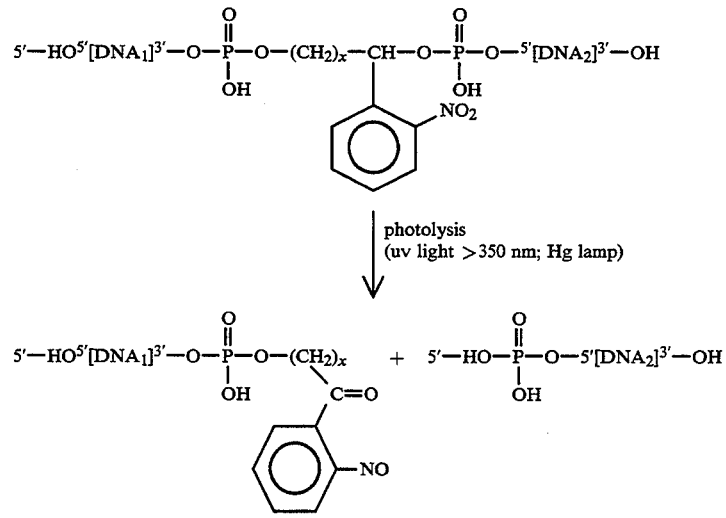

Scheme 4

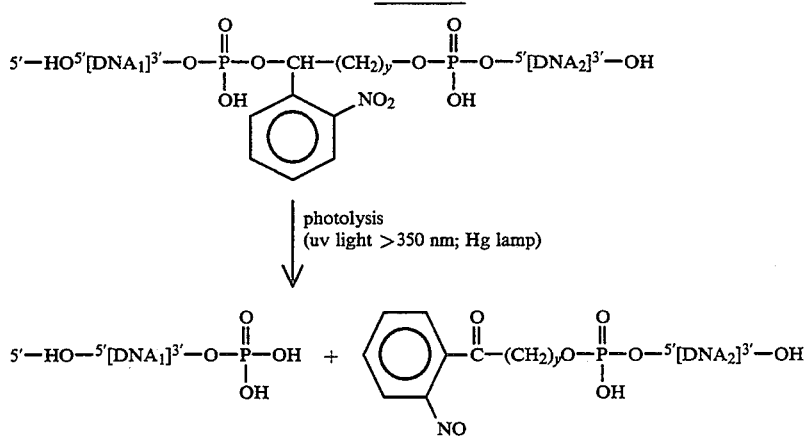

As cleavage is effected via photolysis, using uv light having a wavelength of at least about 350 nm, no enzymatic or chemical reagents are required. Thus, a cleaner procedure is provided, resulting in a product that is necessarily free of contamination with external cleavage reagents. In addition, the polynucleotide reagent itself is inherently more stable, cleavable as it is only by treatment with ultraviolet light of a suitable wavelength.

E. Phosphorylation Using the Above Reagents

The reagents described above, in addition to their utility in providing photolabile cleavage sites, are also useful as chemical phosphorylation reagents. Phosphorylation using these reagents involves condensation with a hydroxyl-containing compound, followed by photochemical cleavage and release of the nitrophenyl group. The novel reagents are quite versatile in this regard, as they may be used for either 5'- or 3'-phosphorylation of a nucleoside or an oligonucleotide chain.

For 5'-phosphorylation, an NP1-type reagent is required, i.e., a reagent wherein x is nonzero and y is zero. As illustrated in Scheme 3 above, cleavage of a polynucleotide reagent containing the NP1-type molecule results in a nucleoside or DNA fragment containing a 5'-phosphate group.

For 3'-phosphorylation, an NP2-type reagent is necessary, as illustrated in Scheme 4. Cleavage of a polynucleotide reagent containing the NP2-type molecule gives rise to cleavage fragments in which one of the fragments contains a 3'-phosphate group and the remaining fragment contains the nitrosophenyl residue.

F. Incorporation of Abasic Sites and Sites for Synthesizing Secondary Oligonucleotide Chains In another embodiment of the invention, reagents are provided which are useful for incorporating abasic sites into oligonucleotide chains, which sites may or may not be "cleavable." These reagents have the structure

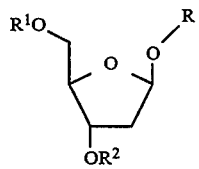

wherein $R^1$ and $R^2$ are as described in part A of this section, above, and wherein R is selected from the group consisting of 2-nitrobenzyl, 4-penten-1-yl,

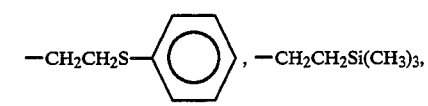

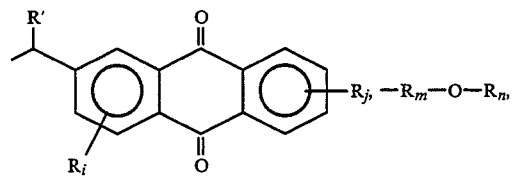

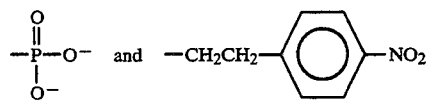

in which R' is hydrogen, aryl or aralkyl, if aryl or aralkyl, preferably $C_1$-$C_8$ aryl or aralkyl, the $R_i$ may be the same or different and are selected from the group consisting of amino, nitro, halogeno, hydroxyl, lower alkyl and lower alkoxy, the $R_j$ may be the same or different and are selected from the group consisting of amino, nitro, halogeno, hydroxyl, lower alkyl and lower alkoxy, i is zero, 1, 2 or 3, j is zero, 1, 2, 3 or 4. $R_n$ represents the levulinyl group —(CO)CH$_2$CH$_2$(CO)CH$_3$ or any other blocking or protective group that can be removed and replaced with hydrogen without affecting $R^1$, such as

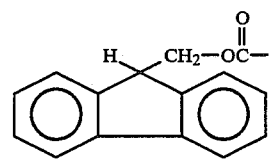

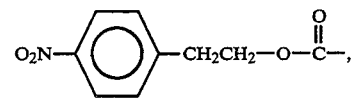

-continued

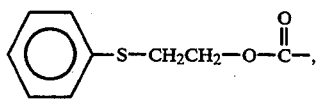

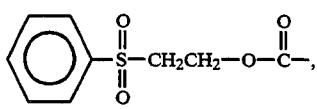

and

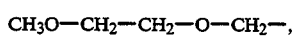

and $R_m$ is either alkylene of 1 to 16, more preferably 2 to 12, carbon atoms, or an oxyethylene oligomer —$(CH_2CH_2O)_z$—, where z is an integer in the range of 1 to 16, more typically 2 to 12, inclusive. Optimally, when R is —$R_m$—O—$R_n$, $R_n$ is levulinyl and $R_m$ is —$(CH_2CH_2O)_4$—. These deoxyribose-based reagents not only introduce abasic sites into an oligonucleotide or polynucleotide chain, but are also, like the reagents described above, useful for providing sites which are cleavable.

Where R is

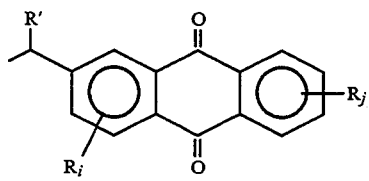

it is preferred that R' be hydrogen or phenyl. The $R_i$ and $R_j$, as indicated, may represent any one of a number of different substituents. In a particularly preferred embodiment, the aforementioned structure is the 2-methylene-9,10-anthraquinone carbonate ester, i.e., $R_i$ and $R_j$ are hydrogen, as is R'. Additional detail on the use of 2-methylene-9,10-anthraquinone moiety as a hydroxyl-protecting group may be found in U.S. patent application Ser. No. 558,881, entitled "Hydroxyl-Protecting Groups Orthogonally Removable by Reduction and Their Use in the Chemical Synthesis of Oligonucleotides," inventors Urdea and Horn, of common assignment with the present application and filed Jul. 27, 1990.

Reagents of the formula

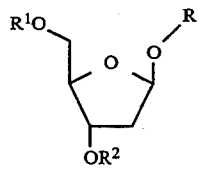

may be readily synthesized from deoxyribose and the alcohol derivative of the R moiety, i.e., R—OH. In the case of 2-nitrobenzyl, for example, deoxyribose would be reacted with 2-nitrobenzyl alcohol to give the 1'-O-(2-nitrobenzyl) derivative. This intermediate may be readily converted into the 5'- and 3'-protected analog using standard methods, e.g., for the incorporation of the dimethoxytrityl (DMT) group or an analogous group at the 5'-position ($R^1$) and a phosphorus derivative such as a phosphoramidite, phosphotriester or the like at the 3'-position ($R^2$).

These reagents may be readily incorporated into an oligonucleotide or polynucleotide chain using standard phosphoramidite chemistry as noted in part D of this section. After incorporation of these deoxyribose-based cleavable moieties into the oligonucleotide or polynucleotide chain, the cleavable chain, containing the abasic sites —OR, will have the structure

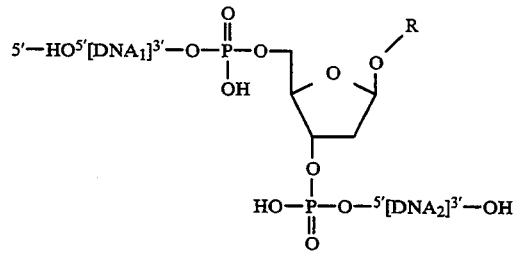

in which $DNA_1$ and $DNA_2$ are first and second segments of DNA as described earlier. Such a polynucleotide reagent may be used in a variety of hybridization assays.

Cleavage of the oligonucleotide or polynucleotide chains containing these reagents may be carried out as follows. Where R is 2-nitrobenzyl, cleavage may be effected via photolysis using uv light having a wave length of at least about 350 nm, followed by basic hydrolysis with, e.g., ammonium hydroxide or the like. Where R is —$CH_2CH_2S$—$\phi$ (wherein $\phi$ represents phenyl), cleavage is effected by oxidation of the sulfur atom to —SO— or $SO_2$— with, e.g., sodium periodate, followed by treatment with base. Where R is —$CH_2CH_2Si(CH_3)_3$, the oligonucleotide may be cleaved by treatment with, for example, fluoride ion, again followed by base. Where R is

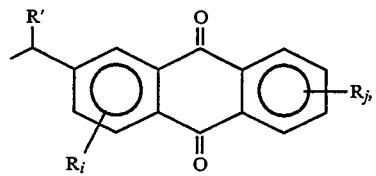

for example, the 2-methylene-9-10-anthraquinone acetal, cleavage may be carried out by oxidation with $Na_2S_2O_4$, followed by treatment with base. Where R is

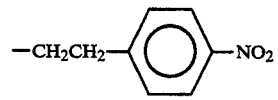

cleavage may be effected using DBU (1,8-diazabicyclo [5.4.0 undec-7-ene]. Where R is phosphate, removal may be effected with alkaline phosphatase followed by treatment with base, while where R is 4-penten-1-yl, cleavage will be carried out typically using Nbromosuccinimide, followed by treatment with base.

As noted above, the reagents of the present invention which enable cleavage of an oligonucleotide or polynucleotide chain may be used in the amplification assays of U.S. patent applications Ser. Nos. 07/252,638 (now abandoned) and 07/340,031, now U.S. Pat. No. 5,124,246 issued Apr. 18, 1989. With the deoxyribose based reagents described in this section, the branch points of the nucleic acid "multimer" may be created using multifunctional nucleic acid monomers having the structure

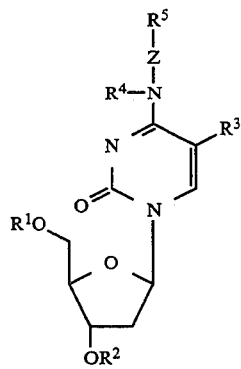

wherein $R^1$ is a base-stable, acid-sensitive blocking group;

$R^2$ is a phosphorus derivative that enables addition of the nucleic acid to the 5'-position of an oligonucleotide chain during chemical synthesis;

$R^3$ is selected from the group consisting of hydrogen, methyl, I, Br and F;

$R^4$ is hydrogen or methyl;

$R^5$ is selected from the group consisting of levulinyl,

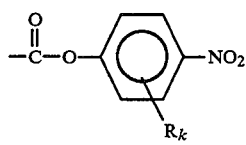

and

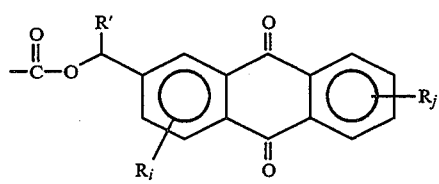

in which R', $R_i$ and $R_j$ are as defined earlier and in which k is 0, 1, 2, 3 or 4, and the $R_k$ may be the same or different and are selected from the group consisting of amino, nitro, halogeno, hydroxyl, lower alkyl and lower alkoxy; and Z is selected from the group consisting of

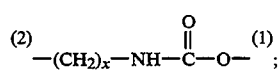

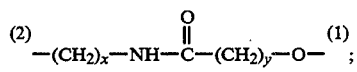

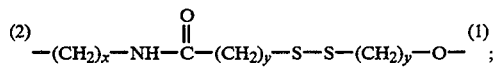

-continued

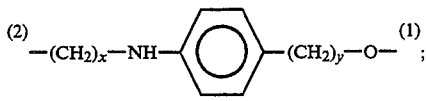

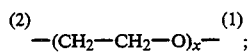

and

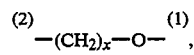

wherein x and y may be the same or different and are integers in the range of 1 to 8.

These nucleic acid monomers may then be incorporated into an oligonucleotide or polynucleotide chain as described above, with the cleavable, or removable, moiety $R^5$ defining the site at which secondary oligonucleotide chains are synthesized. See again co-pending, commonly assigned U.S. patent Application Ser. No. 558,881, cited above.

Branch points of nucleic acid "multireefs" may also be created using multifunctional, non-nucleotidic compounds having the general structure

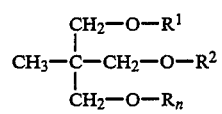

where $R^1$, $R^2$ and $R_n$ are as defined earlier herein. In a particularly preferred embodiment, $R^1$ is DMT, $R^2$ is β-cyanoethyl phosphoramidite, and $R_n$ is levulinyl. Such compounds may be synthesized from tris-hydroxymethyl ethane by: (1) protecting one of the hydroxyl groups by reaction with, e.g., triphenylchlorosilane or tosyl chloride; (2) reacting the protected compound with a salt of $R^2$, e.g., dimethoxytrityl chloride, so that one of the two free hydroxyl groups is converted to —$OR^2$; (3) reacting the compound so provided with $R_n$—OH or a salt of "$R_n$" e g., levulinic acid or a salt thereof, thereby displacing the protecting group of step (1); and (4) reacting the intermediate compound

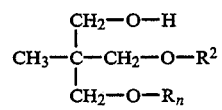

with a reagent effective to convert the remaining free hydroxyl group to —$OR^1$, e.g., β-cyanoethoxy-N,N-diisopropylaminochlorophosphine.

These abasic sites are extremely useful both in enabling cleavage of an oligonucleotide chain at a particular point as well as for other purposes, e.g., synthesis of a branched nucleic acid multimer.

G. Additional Selectable Cleavage Linker Moieties

Still a further reagent useful for providing a selectably cleavable site within an oligonucleotide chain is represented by the structure

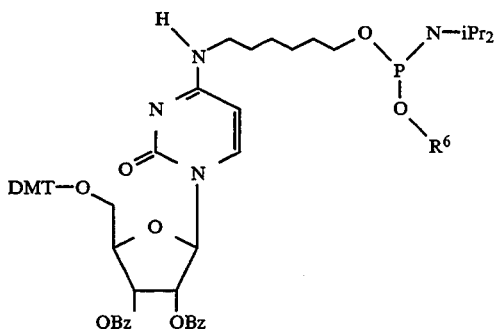

wherein DMT represents dimethoxytrityl, Bz represents benzyl, iPr represents isopropyl, and $R^6$ is either methyl or β-cyanoethyl. As with the reagents described earlier, this moiety may be readily incorporated into an oligonucleotide chain using conventional methods. Cleavage at the site containing this moiety is achieved with a two-step chemical procedure: (1) oxidation with aqueous sodium periodate for 1 hour followed by (2) treatment with aqueous n-propylamine. For further detail, see U.S. patent application Ser. No. 558,897 (now abandoned) for "Large Comb-Type Branched Polynucleotides", of common assignment with the present application, filed Jul. 27, 1990.

It is to be understood that while the invention has been described in conjunction with the preferred specific embodiments thereof, the foregoing description, as well as the examples which follow, are intended to illustrate and not limit the scope of the invention.

EXAMPLE 1

Synthesis of [2-(2-nitrophenyl)-2-(O-dimethoxytrityloxy)ethoxy]-N,N-diisopropylamino-2-cyanoethoxyphosphine ("NP1"): 2-(O-Nitrophenyl)-1,2-ethanediol (2.5 g, 13.6 mmole) was dried by coevaporation once with pyridine. The residue was dissolved in pyridine (50 ml) and 4,4'-dimethoxytrityl chloride (DMTCl) 13.6 mmole was added. The reaction mixture was stirred for 18 hours at 20° C. Most of the pyridine was then distilled off and the oily residue dissolved in 250 ml ethyl acetate. The organic phase was washed with 5% $NaHCO_3$ (2×250 ml), 80% saturated aqueous NaCl (1×250 ml), and dried over solid $Na_2SO_4$. After filtration, the solvent was removed in vacuo and the residue coevaporated with toluene (1×200 ml) and $CH_3CN$ (×200 ml). The product was purified on a column of silica gel (eluted with $CH_2Cl_2$-0.5% triethylamine) to give 6.5 g (13.6 mmole) pure product (100% yield).

The purified product of 1-O-DMT-2-(O-nitrophenyl)-1,2-ethane diol was converted to β-cyanoethyl phosphoramidite by reaction in $CH_2Cl_2$ (50 ml) with chloro-N,N-diisopropylamino-2-cyanoethoxy phosphine (15 mmole) in the presence of diisopropylethylamine (30 mmole) at 10° C. for 30 min. Ethyl acetate (200 ml) was then added and the combined organic phase washed with 80% saturated aqueous NaCl (2×250 ml) and dried over solid $Na_2SO_4$. After removal of the solvent in vacuo, the residue was coevaporated with toluene (100 ml) and $CH_3CN$ (100 ml) to give 9.5 g of the 2-O-phosphoramidite of 1-O-dimethoxytrityl-2-(O-nitrophenyl) -1,2-ethanediol ( 100% yield).

EXAMPLE 2

Synthesis of [2-(2-nitrophenyl)-1-(O-dimethoxytrityloxy)ethoxy]-N,N-diisopropylamino-2 cyano ethoxyphosphine ("NP2"): 2-(O-Nitrophenyl) 1,2-ethane diol (2.5 g, 13.6 mmole) was dried by coevaporation with $CH_3CN$. The dried compound was then dissolved in $CH_2Cl_2$(100 ml) —$CH_3Cl$ (10 ml). N,N-Dimethylaminopyridine (100 mg) and triethylamine (3.6 ml, 26 mmole) were added, and, with stirring, solid t-butyldimethylsilyl chloride (TBDMS-Cl) (2.6 g, 15 mmole) was added. The stirring was continued for 18 hours at 20° C. Then more TBDMS-Cl (200 mg) was added. After one hour the reaction mixture was diluted with 400 ml ethyl acetate. The organic phase was washed with 5% $NaHCO_3$ (2×250 ml) and 80% saturated aqueous NaCl (1×250 ml), and dried over solid $Na_2SO_4$. After removal of the solvents in vacuo, the residue was coevaporated with toluene (200 ml) and $CH_3CN$ (200 ml) to give 2.5 g of crude 1-O-TBDMS-2-(O-nitrophenyl)-1,2ethanediol. The crude material was coevaporated with pyridine, and the residue was dissolved in pyridine (50 ml). DMT-Cl (30 mmole) ws added and the reaction mixture stirred at 20° C. for 48 hours. After removal of the solvent in vacuo, the residue was dissolved in ethyl acetate (250 ml). The organic phase was washed with 5% $NaHCO_3$ (2×250 ml) and 80% saturated aqueous NaCl (1×250 ml), and dried over solid $Na_2SO_4$. After removal of the solvent in vacuo, the residue was coevaporated with toluene and $CH_3CN$. The residue was dissolved in THF (100 ml) and 10 ml of a 1M solution of tetrabutylammonium fluoride in THF was added. The removal of the 1-O-TBDMS group was complete in 30 min. The product was purified on a silica gel column to give pure 2-O-DMT-2-(O-nitrophenyl)-1,2-ethanediol (2.4 g, 4.5 mmole). This material was converted to the 2-cyanoethylphosphoramidite, as described above, in quantitative yield.

EXAMPLE 3

A test fragment 5'-$T_{15}$-3'-p-NP1-p-5'-$T_{20}$-3'-OH ("p"=phosphate) was assembled using standard phosphoramidite synthetic procedures. After complete deprotection, the purified DNA oligomer dissolved in $H_2O$ was subjected to photolysis for 15 minutes (Hg lamp, λ>350 nm). PAGE analysis of the photolyzed sample showed that the treatment had resulted in complete cleavage of the test fragment into new fragments that migrated as would be expected for segments $T_{20}$ and $T_{15}$.

EXAMPLE 4

Synthesis of
5'-DMT-1'-O-(2-nitrobenzyl)-2-deoxyribose
3'-O-methylphosphoramidite:

Deoxyribose (10 mmole), 2-nitrobenzyl alcohol (30 mmole) and dichloroacetic acid ("DCA"; 100 ml) in 100 ml of dry acetonitrile were heated to gentle reflux for 2 hours. After cooling to 20° C. pyridine was added to neutralize the DCA and the solvent removed in vacuo. The residue was dissolved in 500 ml ethyl acetate and the organic phase washed with 400 ml 5% $NaHCO_3$, 400 ml 80% saturated aqueous NaCl and dried over solid $Na_2SO_4$. After filtration the solvent was removed in vacuo and the residue coevaporated with toluene and acetonitrile. The crude reaction mixture was dissolved in $CH_2Cl_2$ and the product was isolated by silica gel chromatography using a 0–6% methanol gradient. The fractions containing the product (mixture of α- and β-isomers; ratio 1:1) were pooled and the solvent removed in vacuo to give 2.5 g of a slightly yellow solid (5.2 mmole; 52% yield).

The residue of deoxyribose-O-nitrobenzyl was dissolved in 25 ml CH$_2$Cl$_2$ containing 200 mg dimethylamino pyridine ("DMAP") and 1.4 ml triethylamine. To this solution was added dropwise DMT-Cl (1.7 g; 5 mmole) dissolved in 25 ml CH$_2$Cl$_2$. When all starting material had been consumed, the reaction mixture was diluted with 250 ml ethyl acetate and extracted, dried and coevaporated as described above. The crude reaction mixture was subjected to silica gel chromatography and the 5,-DMT-1,-O-2-nitrobenzyl-2'-deoxyribose isomers were eluted with a 0–3% methanol gradient to give 2.3 g yellow foam (2.65 mmole).

The 3-methylphosphoramidite was prepared using standard procedures. 5'-DMT-1'-O-(2 nitrobenzyl)-2'-deoxyribose was dissolved in 40 ml CH$_2$Cl$_2$ containing 2.8 ml DiPEA and N,N-diisopropylaminomethylchlorophosphine (2.0 mmole) was added at 0° C. After 30 minutes the reaction mixture was diluted with 200 ml ethyl acetate which was washed with 3×200 ml 80% saturated aqueous NaCl, dried over solid Na$_2$SO$_4$, and filtered. The solvent was removed in vacuo and the residue coevaporated with toluene and acetonitrile. This material was used without further purification.

This protected abasic nucleoside phosphoramidite was incorporated under standard conditions into an oligomer 3'-T$_{20}$-[1'-O-(2-nitrobenzyl)-2'-deoxyribose]-T$_{10}$ on a solid support. The fragment was deprotected with DCA (to remove 5'-DMT), thiophenol (thiophenol/triethylamino/dioxane, 1:1:2 v/v for 1 hour at 20° C., to remove methyl) and NH$_4$OH (aqueous ammonium hydroxide for 1 hour at 20° C., to cleave the 3'-succinate linkage). The supernatant was heated at 60° C. for 18 hours. No cleavage was observed demonstrating the base stability of the 5'-DMT-1'-O-(2 nitrobenzyl)-2'-deoxyribose moiety. A sample of this material in water was subjected to photolysis for 20 minutes using a high intensity Hg lamp to remove the o-nitrobenzyl group from the 5'-DMT-1'-O-(2 nitrobenzyl)-2'-deoxyribose moiety. No cleavage of the oligomer was observed during the photolysis step. A sample of the oligomer which had been subjected to photolysis was incubated in NH$_4$OH at 60° C. for 2 hours. The basic treatment resulted in complete cleavage of the oligomer into the two component oligomers T$_{10}$-3'-p and 5'-p-T$_{20}$.

These reactions are outlined in Schemes 5 and 6.

Scheme 5

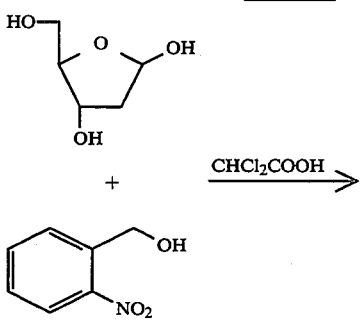

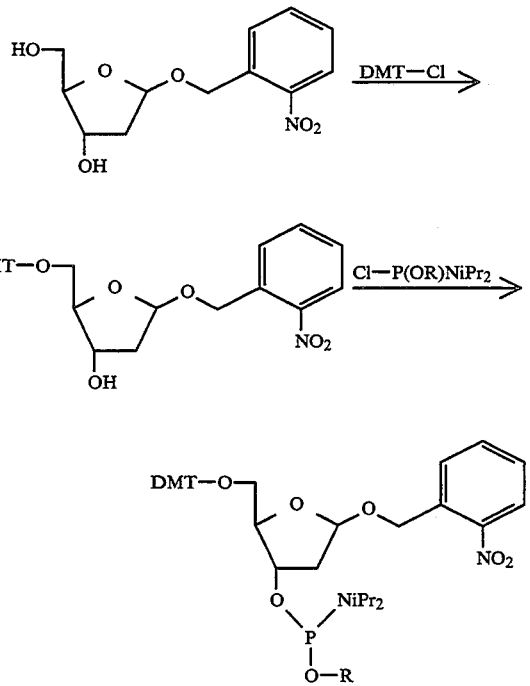

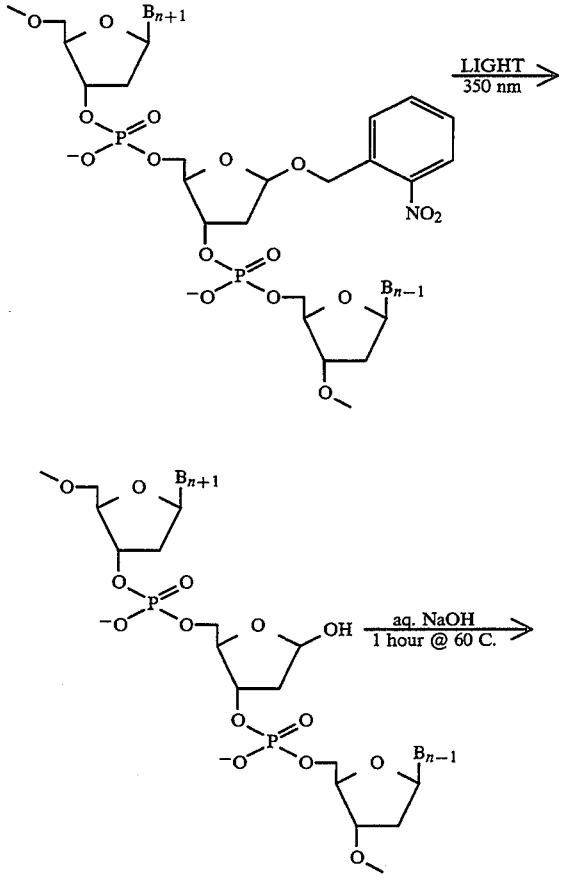

-continued
Scheme 6

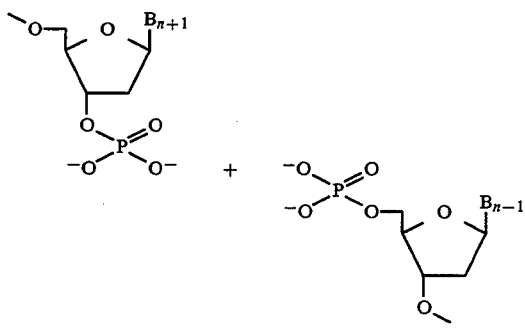

EXAMPLE 5

Preparation of N-4-(O-N,N-diisopropylamino methoxyphosphinyl-6-oxyhexyl)-5'-DMT-2',3'-dibenzoyl cytidine Uridine (24.5 g, 100 mole) was dried by coevaporation with pyridine (2×150 ml). The residue was dissolved in 150 ml of pyridine and dimethoxytrityl chloride-Cl (34 g, 100 mmole) added dropwise with stirring. The reaction mixture was left stirring for 48 hours. Methanol (100 ml) was added and after 30 minutes the solvents were removed in vacuo. The residue was dissolved in 800 ml ethyl acetate and the organic phase was washed with 3×800 ml 5% NaHCO3, 3×800 ml 80% saturated aqueous NaCl, dried over solid Na2SO4, filtered and evaporated to dryness, followed by coevaporation with toluene and acetonitrile. Silica gel chromatography of the crude product using a 0–7% methanol/1% triethylamine gradient afforded 46.36 g, 84.9 mmole of 5'-DMT-ribouridine) was dried by coevaporation with pyridine and the residue was dissolved in 250 ml pyridine. Benzoyl chloride (20 ml, 170 mmole) in 100 ml methylene chloride was added dropwise to the pyridine solution at 0° C. After stirring at 20° C. for 2 hours, the solvent was removed in vacuo and the residue coevaporated with toluene. The residue was dissolved in ethyl acetate and subjected to the same aqueous workup as described above for 5'-DMT-uridine.

The crude 5'-DMT-2',3'-dibenzoyl-uridine, which was used without further purification, was dissolved in 150 ml acetonitrile. 1,2,4-Triazole (88.19 g) was suspended in 400 ml of acetonitrile at 0° C. and POCl3 (27.56 ml) was added with rapid stirring. Then triethylamine (106.7 ml) was added dropwise over 15 minutes to the stirred slurry at 0° C. After 30 minutes, 5'-DMT-2',3'-dibenzoyl-uridine dissolved in 150 ml acetonitrile was added dropwise to the above stirred slurry at 0° C. The ice-water bath was removed and stirring continued for 1° hour at room temperature. The reaction mixture was diluted with 1400 ml ethyl acetate, extracted and dried as above. The solvents were removed in vacuo, coevaporated with toluene then acetonitrile to give 4-(triazolo)-1-b-D-5'-O-DMT-2',3'-dibenzoyl-ribofuranosyl)-2(1H)-pyrimidinone as a white foam in quantitative yield. To a stirred solution of this latter compound in 350 ml CH3CN was directly added solid 6-aminohexanol (11.89 g, 101.5 mmole). Stirring was continued for 18 hours. The reaction mixture was then diluted with 700 ml of ethyl acetate and extracted as above. After drying of the organic phase over Na2SO4, the solvent was removed in vacuo. The product was purified on a silica 60H column eluted with 0–50% of ethyl acetate in CH2Cl2 to give 35.4 g (41.5 mmole) yellow foam of N-4-(6-hydroxyhexyl)-5'-O-DMT-2',3'-dibenzoylcytidine.

The corresponding methylphosphoramidite was prepared using standard procedures. The modified nucleoside N-4-(6-hydroxyhexy-5'-DMT-2',3'-dibenzoyl cytidine (8.7 g, 10.2 mmole) was dissolved in 50 ml methylene chloride containing 8.8 ml (50 mmole) disopropylethylamine and N,N-diisopropylaminomethoxy chlorophosphine (1.94 ml, 10 Mole) was added slowly at 0° C. After 30 minutes the reaction mixture was diluted with 250 ml ethyl acetate and the organic phase was washed with 2×250 ml 5% NaHCO3, 2×80% saturated aq. NaCl, dried over solid Na2SO4 and filtered. The solvent was removed in vacuo and the residue coevaporated with toluene and acetonitrile. The crude phosphitylated material was purified on a column of silica gel using a gradient of 50–70% ethyl acetate in methylene chloride containing 2% triethylamine to give 7.25 g of N-4-(O-N,N-diisopropylaminomethoxy phosphinyl-6-oxyhexyl)-5'-DMT-2',3'-dibenzoyl cytidine

EXAMPLE 6

Oxidative cleavage of the cis-diol system with sodium periodate readily occurs in the terminal ribonucleoside of RNA molecules. In the presence of amines the resulting dialdehyde readily eliminates both the base moiety and the phosphate at the 5'-carbon. This example describes the use of this concept in the design of a cleavable site molecule where two DNA oligomers are linked via the 5'- and the side-chain hydroxyl groups of an N-4-(6-hydroxyhexyl)-cytidine molecule.

The modified ribonucleoside R containing an exocyclic alkyl hydroxyl group was synthesized from uridine. The protected R ribonucleoside phosphoramidite was incorporated under standard conditions into an oligomer 5'-$T_{10}$-R-$T_{15}$-3' on a solid support. Purified samples of the product were subjected to a series of chemical treatments and the samples analyzed by PAGE. No cleavage of the oligomer was observed after treatment with ammonium hydroxide at 60° C. for 18 hours. Treatment with sodium periodate in water at 4° C. for 30 minutes resulted in partial cleavage. Further exposure of periodate-treated oligomer to n-propylamine in triethylammonium acetate at 60° C. for 90 minutes resulted in complete cleavage of the oligomer into $T_{10}$-3'-p and a $T_{15}$ species modified at the 5' end. Scheme 7 outlines the cleavage of R ribonucleoside linked DNA fragments.

The cleavage scheme has been applied to several branched DNA oligomers, where the protected R ribonucleoside phosphoramidite was incorporated during the first cycle of the secondary synthesis of solidsupported linear oligomers containing 10, 20, and 30 comb branch points, respectively. In each case the secondary synthesis was a $T_{10}$ oligomer resulting in branched oligomers of the following structure:

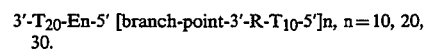

3'-$T_{20}$-En-5' [branch-point-3'-R-$T_{10}$-5']n, n=10, 20, 30.

These molecules were subjected to the cleavage conditions. PAGE analysis indicated that all the side arm oligomers were cleaved off, and $T_{10}$-3'-p was the main product in all cases. The analysis further showed that the product distribution depends on the number of branches in the branched DNA molecule, where the quantity of shorter oligomers increases as more branches are present in the molecule. The decrease in product homogeneity appears to be mainly the result of steric constraints within the solid support during chemical synthesis.

Scheme 7

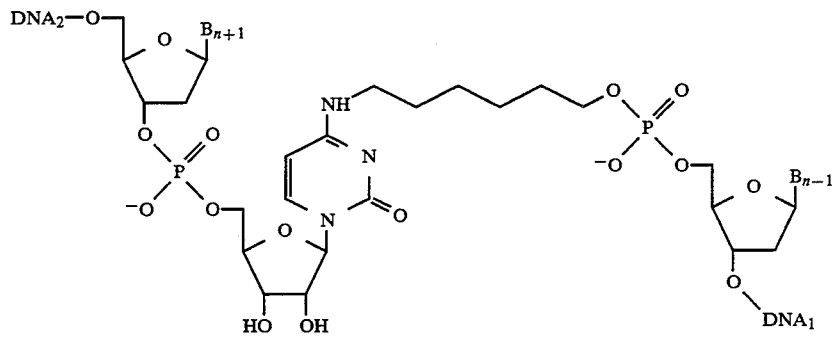

↓ NaIO₄

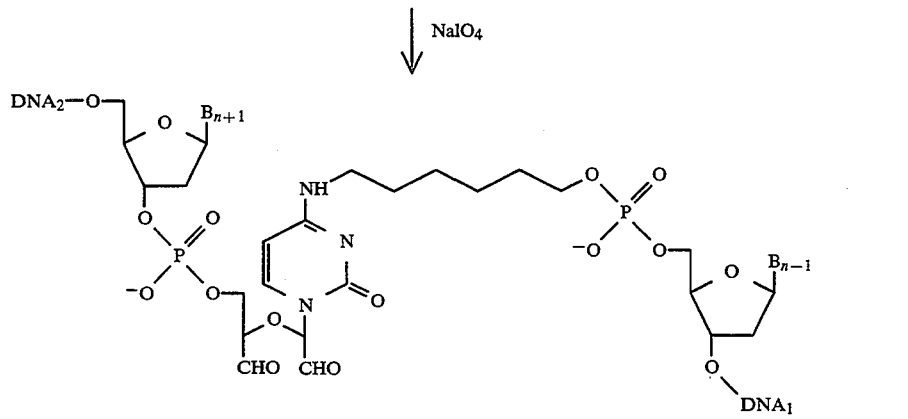

↓ n-PrNH₂/TEAA/1 hr @ 60° C.

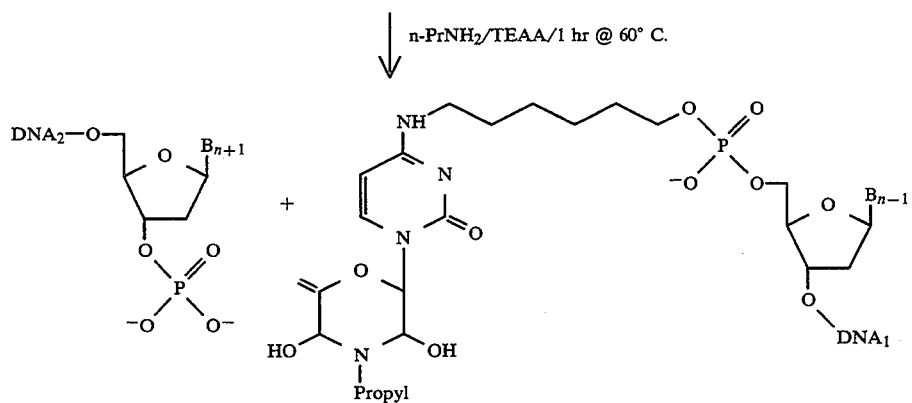

Scheme 8

CH₃—C(CH₂OH)(CH₂OH)—CH₂OH     —TsCl→     CH₃—C(CH₂OH)(CH₂OH)—CH₂—O—Ts
E'                                                                    E' (Ts)

↓ DMT—Cl

EXAMPLE 7

This example describes preparation of the multifunctional linker "DMT-E' (Lev)BCE amidire" as shown in Scheme 8.

25

-continued
Scheme 8

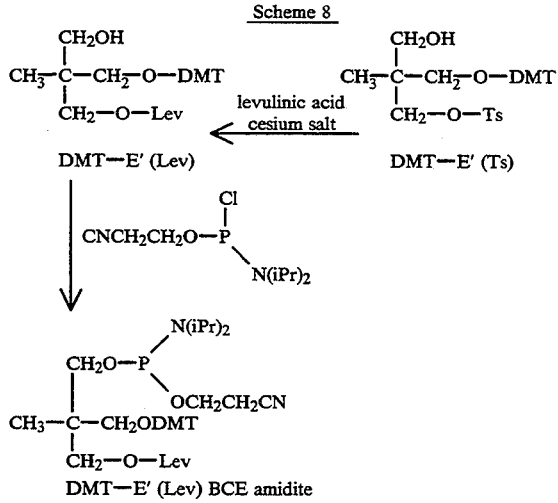

DMT—E′ (Lev) BCE amidite

Tris-hydroxymethyl ethane (E′; 200 mmole) was co-evaporated with 250 ml pyridine and the residue dissolved in 125 ml pyridine. To this solution, cooled to 0° C., was added dropwise a solution of tosyl chloride ("TsCi"; 50 mmole) in 125 ml $CH_2Cl_2$. The reaction mixture was allowed to warm to room temperature and stirring was continued for a total of 5 hours. Then the solvents were removed in vacuo. The residue was dissolved in 500 ml ethyl acetate which was washed with 2×500 ml 5% $NaHCO_3$ solution, 1×500 ml 80% sat. aq. NaCl solution and finally dried over solid $Na_2SO_4$. After filtration the solvent was removed in vacuo to give 13.7 g crude E′(Ts). This material was used without further purification. All E′(Ts) was dissolved in 250 ml $CH_2Cl_2$ and triethylamine (14 ml; 100 mmole) and N,N-dimethylaminopyridine (100 mg) were added. To this solution was added DMT-Cl (13.6 g; 40 mmole) dissolved in 125 ml $CH_2Cl_2$. After 18 hours at room temperature, the reaction mixture was diluted with 500 ml ethyl acetate and subjected to the same aqueous workup as described above.

The crude reaction product was purified on a standard silica column ("800 ml" silica) eluted with a gradient of methanol in $CH_2Cl_2/0.5\%$ triethylamine to give 14.8 g (25 mmole) of pure DMT-E′(Ts). All of this material was treated with 50 mmole of freshly prepared levulinic acid cesium salt (prepared according to M. Bodanszky and A. Bodanszky, in *The Practice of Peptide Synthesis*, p. 37, Springer Verlag (1984)), in 50 ml DMF. The solution was heated on a hot plate in a sealed vial (setting 3; temperature ca. 100° C.) for 18 hours, at which time the analysis showed the reaction to be complete. The DMF was removed in vacuo and the residue dissolved in ethyl acetate. The organic phase was washed as described above. The crude product was subjected to silica gel chromatography and the pure product was eluted with $CH_2Cl_2/0.5\%$ triethylamine to give 2.5 g (4.8 mmole) pure product of DMT-E′(Lev). The pure DMT-E′(Lev) was converted to the 2-cyanoethyl phosphoramidite as follows. DMT-E′(Lev) was dissolved in 20 ml $CH_2Cl_2$ containing N,N-diisopropylethylamine (2.6 ml; 15 Mole) and cooled to 0° C.; to this solution was added under argon with a syringe 2-cyanoethoxy-N,N-diisopropylaminochlorophosphine (1.1 ml; 5 Mole). After ca. 30 minutes the reaction was complete and the reaction mixture was diluted with 150 ml ethyl acetate. The organic phase was washed with

26

2×150 ml 5% $NaHCO_3$ and 2×150 ml 80% saturated NaCl solution. After drying over solid $Na_2SO_4$ the solution was filtered and evaporated to dryness to give 3.6 g white foam of DMT-E′(Lev) BCE amidite. The crude amidite was purified on a column of silica gel eluted with $CH_2Cl_2$/ethyl acetate/triethylamine (45:45:10 v/v) to give a white foam of pure DMT-E′(Lev) BCE amidite (3.24 g; 4.5 mmole). NMR (31p) δ 148.5 ppm and coupling efficiency 98%.

EXAMPLE 8

This example describes an alternative synthesis of the multifunctional linker "DMT-E′ (Lev) BCE amidite"as shown in Scheme 9.

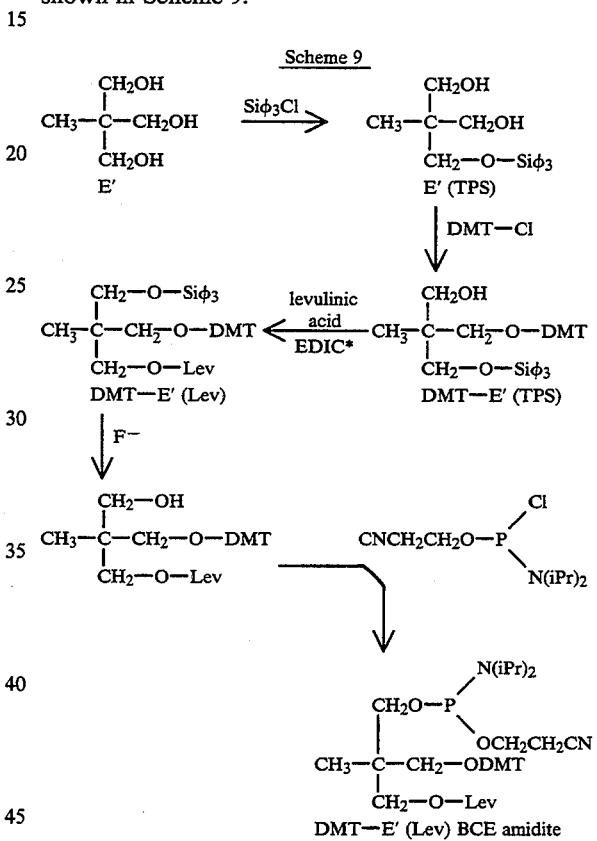

*EDIC = 1-ethyl-3-(3-dimethylaminopropyl) carbodiimide hydrochloride.

Tris-hydroxymethyl ethane (200 mmole) was co-evaporated with 250 ml pyridine and the residue dissolved in 125 ml pyridine. To this solution, cooled to 0° C., was added dropwise a solution of triphenylchlorosilane ("TPS"; 50 mmole) in 125 ml $CH_2Cl_2$. The reaction mixture was allowed to warm to room temperature and stirring was continued for a total of 18 hours. Then the solvents were removed in vacuo. The residue was dissolved in 500 ml ethyl acetate which was washed with 2×500 ml 5% $NaHCO_3$ solution, 1×500 ml 80% sat. aq. NaCl solution and finally dried over solid $Na_2SO_4$. After filtration the solvent was removed in vacuo to give 18 g crude E′ (TPS). This material was used without further purification. All E′(TPS) (46 mmole) was dissolved in 250 ml $CH_2Cl_2$ and triethylamine (14 ml; 100 mmole) and N,N-dimethylaminopyridine (100 mg) were added. To this solution was added DMT-Cl (50 mmole) dissolved in 125 ml $CH_2Cl_2$. After 18 hours at room temperature, the reaction mixture was diluted with 500 ml ethyl acetate and subjected to the same aqueous workup as described above to give 35.8 g yellow foam.

The crude reaction product was purified on a standard silica column ("800 ml" silica) eluted with a gradient of methanol in $CH_2Cl_2$/0.5% triethylamine to give 14.8 g (25 mmole) of pure DMT-E'(TPS). Purified DMT-E'(TPS) (10 Mole) was dissolved in 50 ml containing N,N-dimethylaminopyridine (100 mg) and 2,6-lutindine (2.3 ml, 20 mmole), and levulinic acid (2.3 g, 20 mmole) was added. To this solution was added dropwise 1-ethyl-3-(3-dimethylaminopropyl)carbodiimide hydrochloride (3.83 g, 20 mmole) dissolved in 50 ml $CH_2Cl_2$. After 18 hours the reaction was complete (tlc analysis), and the reaction mixture was diluted with 500 ml ethyl acetate and subjected to the same aqueous workup as described above. The residue from this workup was dissolved in THF (50 ml) and first 40 ml pyridine and then 10 ml concentrated acetic acid were added, followed by 20 ml 1M tetrabutylammonium fluoride in THF (Aldrich). Tlc analysis after 30 minutes showed that all starting material had been consumed. Most of the solvent was then removed in vacuo and the remaining residue subjected to the following aqueous workup: ethyl acetate (250 ml) was added to dissolve most organic material and 250 ml 5% sodium bicarbonate solution was added slowly ($CO_2$ evolution). Then solid $NaHCO_3$ was added with stirring and dissolved until solid salt remained and $CO_2$ evolution ceased. The combined aqueous/organic solution was transferred to a separatory funnel and the organic phase washed as described above. Removal of the solvent yielded 5.96 g crude DMT-E'(Lev), as a clear oil. The product was isolated by silica gel chromatography using ca. 500 g silica and $CH_2Cl_2$/0.25% triethylamine containing 0% and 1% methanol as the eluent to give 2.7 g (5.2 mmole) DMT-E'(Lev) as a clear, colorless oil.

The pure DMT-E'(Lev) was converted to the 2-cyanoethyl phosphoramidite as follows: DMT-E'(Lev) was dissolved in 20 ml $CH_2Cl_2$ containing N,N-diisopropylethylamine (2.6 ml; 15 mmole) and cooled to 0° C.; to this solution was added under argon with a syringe 2-cyanoethoxy-N,N-diisopropylamino-chlorophosphine (1.1 ml; 5 mmole). After ca. 30 minutes the reaction was complete and the reaction mixture was diluted with 150 ml ethyl acetate. The organic phase was washed with 2×150 ml 5% $NaHCO_3$ and 2×150 ml 80% saturated NaCl solution. After drying over solid $Na_2SO_4$ the solution was filtered and evaporated to dryness to give 3.4 g white foam of DMT-E'(Lev) BCE amidite. The crude amidite was purified on a column of silica gel eluted with $CH_2Cl_2$/ethyl acetate/triethylamine (45:45:10 v/v) to give a white foam of pure DMT-E'(Lev) BCE amidite (2.4 g; 3.3 mmole). NMR ($^{31}P$) δ 148.5 ppm and coupling efficiency 98%.

We claim:

1. A polynucleotide reagent having the structure

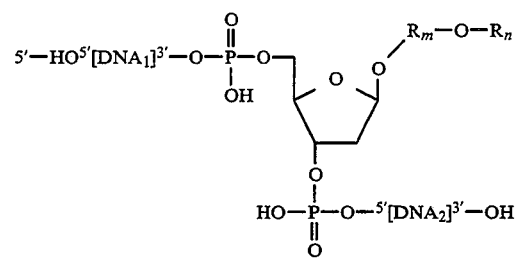

wherein
DNA$_1$ is a first segment of DNA;
DNA$_2$ is a second segment of DNA; and
R$_m$ is $C_1$-$C_{16}$ alkylene or an oxyethylene oligomer —(CH$_2$CH$_2$O)$_z$— where z is an integer in the range of 1 to 16 inclusive, and R$_n$ is selected from the group consisting of

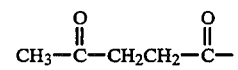

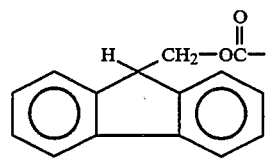

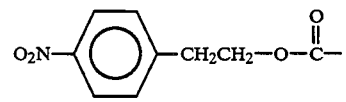

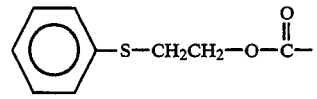

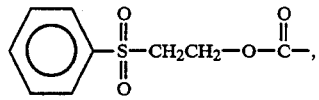

and $CH_3O-CH_2-CH_2-O-CH_2-$.

2. The polynucleotide reagent of claim 1, wherein R$_m$ is —(CH$_2$CH$_2$O)$_4$— and R$_n$ is

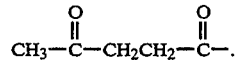

3. The polynucleotide reagent of claim 2, wherein R$_m$ is $C_1$-$C_{16}$ alkylene.

4. The polynucleotide reagent of claim 1, wherein R$_m$ is $C_2$-$C_{12}$ alkylene.

5. The polynucleotide reagent of claim 1, wherein R$_m$ is an oxyethylene oligomer —(CH$_2$CH$_2$O)$_z$— where z is an integer in the range of 2 to 12 inclusive.

6. The polynucleotide reagent of claim 1, wherein R$_n$ is

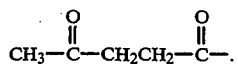

7. The polynucleotide reagent of claim 4, wherein $R_n$ is

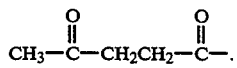

8. The polynucleotide reagent of claim 5, wherein $R_n$ is

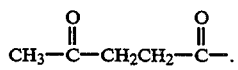

9. The polynucleotide reagent of claim 1, wherein $R_n$ is

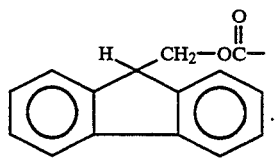

10. The polynucleotide reagent of claim 4, wherein $R_n$ is

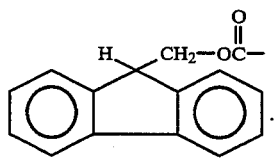

11. The polynucleotide reagent of claim 5, wherein $R_n$ is

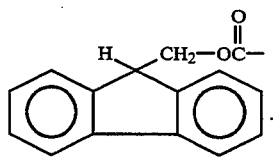

12. The polynucleotide reagent of claim 1, wherein $R_n$ is

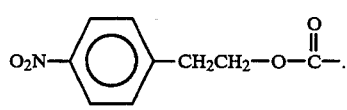

13. The polynucleotide reagent of claim 4, wherein $R_n$ is

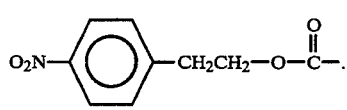

14. The polynucleotide reagent of claim 5, wherein $R_n$ is

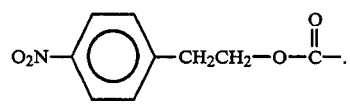

15. The polynucleotide reagent of claim 1, wherein $R_n$ is

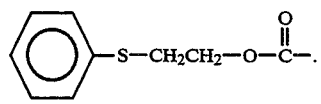

16. The polynucleotide reagent of claim 4, wherein $R_n$ is

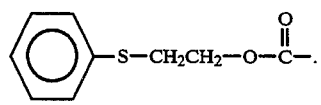

17. The polynucleotide reagent of claim 5, wherein $R_n$ is

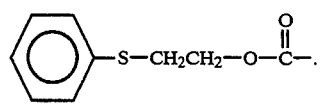

18. The polynucleotide reagent of claim 1, wherein $R_n$ is

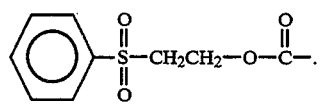

19. The polynucleotide reagent of claim 4, wherein $R_n$ is

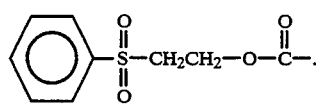

20. The polynucleotide reagent of claim 5, wherein $R_n$ is

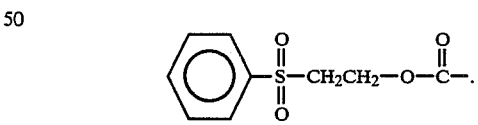

21. The polynucleotide reagent of claim 1, wherein $R_n$ is $CH_3O-CH_2-CH_2-O-CH_2-$

22. The polynucleotide reagent of claim 4, wherein $R_n$ is $CH_3O-CH_2-CH_2-O-CH_2-$

23. The polynucleotide reagent of claim 5, wherein $R_n$ is $CH_3O-CH_2-CH_2-O-CH_2-$

* * * * *